United States Patent [19]

Tsaur

[11] Patent Number: 5,858,939
[45] Date of Patent: *Jan. 12, 1999

[54] METHOD FOR PREPARING BARS COMPRISING USE OF SEPARATE BAR ADJUVANT COMPOSITIONS COMPRISING BENEFIT AGENT AND DEPOSITION POLYMER

[75] Inventor: Liang Sheng Tsaur, Norwood, N.J.

[73] Assignee: Lever Brothers Company, Division of Conopco, Inc., New York, N.Y.

[*] Notice: The term of this patent shall not extend beyond the expiration date of Pat. No. 5,770,556.

[21] Appl. No.: 821,504

[22] Filed: Mar. 21, 1997

[51] Int. Cl.⁶ .................................................. C11D 11/00
[52] U.S. Cl. .......................... 510/141; 510/155; 510/156; 510/447; 510/450; 510/475; 510/495; 510/496; 510/504
[58] Field of Search ...................................... 510/141, 130, 510/155, 156, 447, 450, 475, 495, 496, 498, 504

[56] References Cited

U.S. PATENT DOCUMENTS

| | | | |
|---|---|---|---|
| 3,761,418 | 9/1973 | Parran, Jr. ................. | 510/382 |
| 3,814,698 | 6/1974 | Ferrara ..................... | 510/152 |
| 4,234,464 | 11/1980 | Morshauser .............. | 510/141 |
| 4,673,525 | 6/1987 | Small ........................ | 510/151 |
| 4,788,006 | 11/1988 | Bolich, Jr. et al. ....... | 510/121 |
| 4,820,447 | 4/1989 | Medcalf .................... | 510/151 |
| 4,948,576 | 8/1990 | Verdicchio et al. ...... | 424/59 |
| 5,037,818 | 8/1991 | Sime ......................... | 514/183 |
| 5,064,555 | 11/1991 | Medcalf, Jr. et al. .... | 510/156 |
| 5,096,608 | 3/1992 | Small ........................ | 510/153 |
| 5,098,608 | 3/1992 | Miyazawa et al. ....... | 510/147 |
| 5,154,849 | 10/1992 | Visscher et al. ......... | 510/150 |
| 5,300,249 | 4/1994 | Schwartz et al. ........ | 510/153 |
| 5,372,751 | 12/1994 | Rys-Cicciari et al. ... | 510/155 |
| 5,478,501 | 12/1995 | Rau ........................... | 510/135 |
| 5,494,612 | 2/1996 | Finucane .................. | 510/155 |
| 5,681,980 | 10/1997 | Beerse et al. ............ | 510/152 |
| 5,703,026 | 12/1997 | Setser et al. ............. | 510/152 |

FOREIGN PATENT DOCUMENTS

94/03152  2/1994  WIPO .

*Primary Examiner*—Paul Lieberman
*Assistant Examiner*—Lorna M. Douyon
*Attorney, Agent, or Firm*—Ronald A. Koatz

[57] ABSTRACT

A method of enhancing deposition of benefit agent from bars which method comprises separately preparing an adjuvant composition comprising benefit agent and deposition polymer (e.g., cationic polymer); and base bar composition comprising a surfactant system, wherein the adjuvant composition is initially prepared by mixing components forming the adjuvant composition and water to form a uniform aqueous mixture containing benefit agents having particle size of 0.1 $\mu$m to 100 $\mu$m and drying said aqueous mixture to form a dried adjuvant composition. By combining adjuvant compositions separately from the base bar composition, it is possible to create a final bar having enhanced deposition of benefit agent without compromising processing or consumer attributes (e.g., foaming).

10 Claims, No Drawings

METHOD FOR PREPARING BARS COMPRISING USE OF SEPARATE BAR ADJUVANT COMPOSITIONS COMPRISING BENEFIT AGENT AND DEPOSITION POLYMER

FIELD OF THE INVENTION

The present invention relates to a method of enhancing deposition of benefit agent from bar compositions using adjuvant compositions. Specifically benefit adjuvants containing benefit agent and deposition polymer are separately formed and mixed with surfactant containing chips to form final bars. Using benefit adjuvant compositions, applicants are able to deliver perceivable skin benefit without negatively affecting bar processing and without compromising lather performance. In a second embodiment, the invention relates to bars prepared using said adjuvant compositions.

BACKGROUND

It is difficult to formulate a personal wash bar which can deliver sufficient skin benefit agent onto skin to provide a perceivable skin benefit and which does not at the same time affect bar processing (e.g., benefit agent may be sticky and clog machinery or may be of high viscosity and render the bar composition difficult to extrude) and/or affect bar user properties (e.g., foaming).

For example, soap bars containing high levels of oils have been claimed in U.S. Pat. No. 3,814,698 to Ferrara et al. However, such soap bars tend to reduce lather performance, are soft and become softer with increased use which makes the bars difficult to use and undesirable to handle. Besides the above undesirable properties, soap bars containing high level of oils are soft and mushy resulting in difficulties in processing through conventional bar extrusion equipment.

Unexpectedly, applicants have found that when the benefit agents are separately incorporated into bars as part of a bar adjuvant comprising (1) benefit agent; (2) a deposition polymer aid (e.g., cationic polymer); and (3) an optional water soluble or dispersible material (e.g., to manipulate rigidity, flowability and dispersibility of additive), enhanced deposition of benefit agent is achieved without affecting processing or comprising lather volume.

The use of deposition polymers, such as cationic polymers, to enhance deposition of a water insoluble particle (e.g., silicone oil) is known in the context of deposition from liquid shampoo onto hair. U.S. Pat. No. 5,037,818 to Sime, for example, teaches cationics to enhance deposition on hair from shampoos.

WO 94/03152 (assigned to Unilever PLC) teaches liquid cleansers that can effectively deposit silicone oil on skin using cationic polymers.

U.S. Pat. No. 4,788,006 to Bolich, Jr. et al. teaches shampoos with silicone particles of 2 to 50 micrometers which compositions contain xanthan gum to condition hair.

None of the above references, however, relate to deposition of benefit agent from bars onto skin using cationic polymers, let alone the use of specific adjuvant compositions comprising benefit agent, deposition aid (e.g., cationic) and optional water soluble or water dispersible materials, wherein the adjuvants can deliver benefits without compromising bar processing and/or bar use properties.

The art has disclosed personal cleansing bars containing conditioning bath oils (see for example, U.S. Pat. No. 3,814,698 to Ferrara). The conditioning oils, however, reduce sudsing and lathering, create processing difficulties in plodding and stamping and are not deposited in compounds sufficient to provide a perceivable skin effect.

The art also discloses personal washing bars comprising cationic polymers to provide a skin conditioning effect and/or mildness (see U.S. Pat. No. 4,673,525 to Small et al.; U.S. Pat. No. 4,820,447 to Medcalf, Jr. et al.; and U.S. Pat. No. 5,096,608 to Small et al.). The cationic is not added to a separate adjuvant powder/chip which is then mixed in with a base chip prior to plodding and extrusion to form final bar. While not wishing to be bound by theory, it is believed to be this formation of a separate concentrated region prior to mixing with base chip which allow enhanced deposition to occur in the subject invention compared to the reference.

U.S. Pat. No. 3,761,418 to Parran, Jr. discloses detergent compositions containing both water insoluble particulate substances and cationic polymers to enhance deposition and retention of the particulate substances on surfaces washed with detergent composition. Specifically, enhanced deposition of antimircobial agents from toilet detergent bar using cationic polymers is disclosed. Again the reference does not teach or suggest the use of cationic polymer and benefit agent in a separate chip/powder prior to mixed with base chip.

In summary, it is known that deposition of water insoluble particles from personal cleansing product can be enhanced using cationic (e.g., use of cationic to enhance antimicrobial deposition from detergent bar). However, when cationic has been used to enhance deposition of oil, deposition has been small and not sufficient for perceivable skin effect. This is because cationic and benefit agent/oil have never been physically separated from the rest of the composition prior to final formation of bar.

Unexpectedly, applicants have found that when benefit agent and cationic polymer are separately formed and later mixed with other bar components, enhanced deposition is obtained. Further, bars prepared using adjuvant chips/powders can be readily processed by conventional bar processes and lather properties are not compromised.

Finally, applicants note that in a copending application U.S. Ser. No. 08/821,501, filed same day as subject application, entitled "Process for Making Bar Compositions Having Enhanced Deposition of Benefit Agent Comprising Use of Specific Spray-Dryable Adjuvant Powders", applicants teach use of a separately prepared adjuvant powder to be mixed with surfactant-containing base chips. The adjuvant of that invention, however, comprise carriers of minimum melting point (80° C. and higher, preferably about 100° C.) and can be prepared only by spray-drying. By contrast, adjuvants of the subject invention can be prepared by spray-drying, freeze-drying and other forms of drying.

BRIEF SUMMARY OF THE INVENTION

The present invention relates to a method of enhancing deposition of benefit agents from bars which method comprises separately preparing (1) adjuvant compositions comprising a benefit agent, deposition polymer and optionally water soluble or water dispersible polymer and (2) "base" surfactant containing compositions.

The adjuvant compositions of the invention comprise:
  20% to 96%, preferably 30% to 60% by wt. composition benefit agent;
  2% to 40%, preferably 5% to 30% by wt. composition cationic polymer;
  0% to 78% by wt. composition water soluble water dispersible filler;

0% to 15% by wt. composition water.

The final bars of the invention comprise about 5 to 50%, preferably 15 to 35% by wt. of total bar composition the adjuvant compositions disclosed above.

In a second embodiment, the invention relates to a process for making the adjuvant composition of the invention comprising mixing benefit agent, deposition polymer and optional water soluble/dispersible agent; and drying said mixture (e.g., via freeze drying, spray-drying or roller drying) to form solid or semisolid adjuvants.

DETAILED DESCRIPTION OF THE INVENTION

The present invention relates to a method of enhancing deposition of benefit agents which method comprises separately preparing from bars adjuvant bar compositions comprising benefit agent, deposition aid (e.g., cationic polymer) and optional water soluble/water dispersible materials. The adjuvants are mixed with "base" bar compositions, plodded, extruded and stamped to form final bars or they are mixed with molten base bar compositions and solidified to form a bar.

The invention is further concerned with bar compositions comprising a mixture of (a) the benefit agent composition and (b) said "base" (comprising primarily a surfactant system).

Each of the separate adjuvant and base bar compositions is described in more detail below.

ADJUVANT COMPOSITIONS

The adjuvant composition of the invention (as noted, benefit agent and deposition polymer must be added as separate adjuvant composition rather than be added as individual components with other final bar ingredients at initial mixing) have the following composition:

(1) 20% to 96% by wt. composition benefit agent;

(2) 2% to 40%, preferably 5% to 30% by wt. composition deposition (e.g., cationic) polymer;

(3) 0% to 78% by wt. composition water soluble or water dispersible filler; and (4) 0% to 15% by wt. composition water.

Benefit Agent Composition

The benefit agent "composition" of the subject invention may be a single benefit agent component or it may be a benefit agent compound added via a carrier. Further the benefit agent composition may be a mixture of two or more compounds. In this case a mixture of oil and solid compound is not preferred because a combination of oil with hydrophobic solid particles can work as antifoamer which tend to reduce lather of bars containing this kind of benefit adjuvants. In addition, the benefit agent itself may act as a carrier for other components one may wish to add to the bar composition.

The benefit agent can be an "emollient oil" by which is meant a substance which softens the skin (stratum corneum) by increasing its water content and keeping it soft by retarding decrease of water content.

Preferred emollients include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, petrolatum, microcrystalline wax, ceresin, squalene, pristan and mineral oil;

(f) higher fatty acids such as lauric, myristic, palmitic, stearic, behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids; and (n) mixtures of any of the foregoing components.

Particularly preferred benefit agents are silicone oil, petrolatum and vegetable oils, preferably having viscosity greater than about 1,000 centipoise. The silicone may be a gum and/or it may be a mixture of silicones, also preferably having viscosity greater than 1,000 centistoke. One example is polydimethylsiloxane having viscosity of about 60,000 centistokes.

The benefit agent generally comprises about 20% to 96%, preferably 30% to 80% by weight of the adjuvant composition.

Deposition Polymer

The deposition polymer can be cationic polymers or amphoteric polymers with excess positive charge. Examples of deposition polymers suitable for the adjuvant composition are described in WO 94/03152, WO 93/04161, WO 93/21293, U.S. Pat. Nos. 4,299,494 and 4,272,515. These are cationic guar gums derivatives which are commercially available under the trade name Jaguar® from Rhone-Poulenc such as Jaguar C13S, Jaguar C16, Jaguar C14S or Jaguar C17; those under the trade name N-Hance® from Hercules such as N-Hance 3215, N-Hance 3196 or N-Hance 3000; and cationic cellulose ethers which are available from Union Carbide under the trade name Polymer JR®. Other preferred cationic polymers are synthetic cationic polymers such as dimethyl dialkyl ammonium chloride homo- or copolymers available under the trade name Merquat® 100 or Merquat® 550, dimethyldialkyl ammonium chloride acrylic acid amphoteric polymers available under the trade name Merquet® 280 ex Calgon Corp., cationic polyacylamides such as Salcare® from Allied Colloids Inc., and cationic vinyl pyrrolidone copolymers such as Gafquat® 755 from GAF Corp.

Still other cationics include Mirapol polymer such as Mirapol A15® by Miranol Chemicals, and cationic starch such as StaLok 300 and 400® made by Staley, Inc.

The deposition polymer may comprise 2% to 40% by wt., preferably 5% to 30% of the adjuvant composition.

Water Soluble/Dispersible Filler

The water soluble/dispersible filler generally comprises the portion of the adjuvant not made of the benefit agent and deposition polymer.

The filler is used to modify the adjuvant's physical properties such as flowability, rigidity, water sensitivity and water dispersity. The adjuvant of this invention are preferred to be solid or semi-solid materials that are not tacky, easy to handle and to process, and capable of maintaining their integrity under conditions of bar processing. After incorporating into the bar, the adjuvant should exist in the bar as discrete particles concentrated with both skin benefit agents and depositions polymers to more effectively deliver the benefit agents onto the skin during the use of the bar. To prevent gritty, tacky and other non-desirable bar in-use properties, the discrete adjuvant particles can be modified using the water soluble or dispersible filler.

Specifically the required adjuvant processing and in-use physical properties can be achieved by varying the level and the type of fillers contained in the adjuvants.

A variety of water soluble or dispersible materials can be utilized as fillers for these purposes. The fillers are referred to as solid materials, especially when the benefit agents are oily materials. Examples of water soluble or dispersible materials that are useful as property modifying fillers include (1) anionic, nonionic or amphoteric surfactants that are suitable for personal cleansing applications such as alkyl ether sulfate, cocoylisethionate, or cocoylaminopropyl betaine; (2) high molecular weight nonionic materials such as polyethylene glycol sold by Union Carbide under the trade name Carbowax®, polyvinyl alcohol sold by Air Product under the trade name Airvol®, polyvinyl pyrrolidone from ISP Technologies, Inc., maltodextrin or modified corn starch sold under the trade name Capsul® or Purity Gum Bee® by National Starch & Chemicals, cellulose ether from Dow Chemical sold under the name of Methocel® or Nitrosol® from Aqualon; (3) inorganic or organic salts such as sodium and magnesium sulfate, citrate or; (4) water dispersible organic or inorganic solid particles, such as silica, silicates, talc, calcite, kaolin, fatty acids, waxes, starch and insoluble salt of fatty acids with size less than 10 $\mu$m, preferably less than 5 $\mu$m.

Optionals

Other materials which may be optionally found in the adjuvant compositions are polyols such as glycerine or propylene glycol and additional surfactants, including amphoteric surfactants such as cocoamidopropyl betaine.

The adjuvant composition may additionally comprise 0% to 15%, preferably 1% to 10% water.

Adjuvant Preparation

Generally, the adjuvant is prepared by mixing all the components with water to form a uniform aqueous mixture. The mixture is then dried, i.e., freeze dried, spray dried or roller dried to form a solid or semi-solid material. The benefit agents can be added into the aqueous mixture as pure ingredients or as emulsions. The size of benefit agents in the aqueous mixture before drying should be in the range of 100 $\mu$m to 0.1 $\mu$m, preferably in the range of 50 $\mu$m to 0.1 $\mu$m for non-solid benefit agents such as silicone oils or petrolatum, and in the range of 10 $\mu$m to 0.1 $\mu$m for solid benefit agents such as fatty acids or waxes.

BASE BAR COMPOSITION

The invention comprises bar compositions in which 5 to 50% by wt., preferably 10% to 35% of the bar is adjuvant compositions as described above, and 95% to 50% of the bar comprises a "base" composition which generally comprise the surfactant system defining the final bar. The base composition can be solid if the bar is made by extrusion process or molten liquid if the bar is made, for example, by melt casting process.

Specifically, the surfactant system "base" composition comprises about 30% to 90% by wt. of a surfactant system wherein the surfactant is selected from the group consisting of soap (pure soap surfactant systems are included), anionic surfactant, nonionic surfactant, amphoteric/zwitterionic surfactant, cationic surfactant and mixtures thereof. These chips may additionally comprise other components typically found in final bar compositions, for example, minor amounts of fragrance, preservative, opacifier, skin feel polymer etc.

Surfactant System

The term "soap" is used herein in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural or synthetic aliphatic (alkanoic or alkenoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12 to 18 carbon atoms.

Coconut oil employed for the soap may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil, in which case the fatty acid content is about 85% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). among the alkyl ether sulfates are those having the formula:

$$RO(CH_2CH_2O)_n SO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

$$R^4 O_2 CCH_2CH(SO_3M)CO_2M;\text{ and}$$

amide-MEA sulfosuccinates of the formula;

$$R^4 CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$R^1 CON(CH_3)CH_2CO_2M,$$

wherein $R^1$ ranges from $C_8$–$C_{20}$ alkyl and M is a solubilizing cation.

Taurates are generally identified by formula:

$$R^2 CONR^3 CH_2CH_2SO_3M$$

wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of the total bar composition. Preferably, this component is present from about 30% to about 60%.

The acyl isethionate may be an alkoxylated isethionate such as is described in Ilardi et al., U.S. Pat. No. 5,393,466, hereby incorporated by reference. This compound has the general formula:

$$\underset{\|}{RC}\underset{O}{}-O-\underset{|}{CH}\underset{X}{}-CH_2-(O\underset{|}{CH}\underset{Y}{}-CH_2)_m-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1-[-\underset{\|}{C}\underset{O}{}-NH(CH_2)_n-]_n-\underset{|}{\underset{R^3}{N^+}}-X-Y \quad \underset{}{R^2}$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

m is 2 to 4;

n is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

$$R^1-\underset{|}{\underset{R^3}{N^+}}-CH_2CO_2^- \quad R^2$$

and amido betaines of formula:

$$R^1-CONH(CH_2)_n-\underset{|}{\underset{R^3}{N^+}}-CH_2CO_2^- \quad R^2$$

where n is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

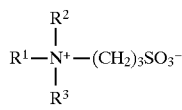

or

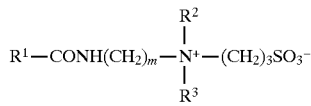

where m is 2 or 3, or variants of these in which —(CH$_2$)$_3$SO$_3^-$ is replaced by

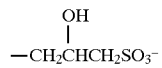

In these formulae R$^1$, R$^2$ and R$^3$ are as discussed previously.

The nonionic which may be used as the second component of the invention include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl (C$_6$–C$_{22}$) phenols ethylene oxide condensates, the condensation products of aliphatic (C$_8$–C$_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which are also incorporated into the subject application by reference.

Although the bar may be a pure soap bar, preferably the surfactant system of this chip (forming the surfactant system in the bar) comprises:

(a) a first synthetic surfactant which is anionic; and
(b) a second synthetic surfactant selected from the group consisting of a second anionic different from the first, a nonionic, an amphoteric and mixtures thereof.

The first anionic can be any of those recited above, but is preferably a C8 to C$_{18}$ isethionate as discussed above. Preferably acyl isethionate will comprise 10% to 90% by wt., preferably 10% to 70% total bar composition.

The second surfactant is preferably a sulfosuccinate, a betaine or mixtures of the two. The second surfactant or mixture of surfactant will generally comprise 1% to 10% total bar composition. A particularly preferred composition comprises enough sulfosuccinate to form 3–8% total bar compositions and enough betaine to form 1–5% of total bar composition.

Processing to Form Final Bar

In general, the moisturizing cleaning bar of the present invention may be made by conventional techniques known in the art such as extrusion, melt-casting or freezing process. A preferred process for preparing the final bar of the invention is the extrusion process which comprises the steps of combining, drying, amalgamating, milling, plodding and stamping. In this process, the adjuvant compositions described above can be added to and mixed with the surfactant "base" compositions and other bar additives before plodding, such as in the amalgamating or milling stage. The premix is then extruded through the plodder and stamped to form the bar of the invention. Another preferred process is a melt casting/freezing process in which surfactants and other bar ingredients are mixed at high temperature to form a flowable molten fluid. The molten fluid is then pumped to or injected into a cold mold to solidify inside the mold to form a bar. In this process, the benefit adjuvant can be added into the molten fluid as dispersed particles before it solidifies.

The following examples are intended to further illustrate the invention and are not intended to limit the invention in any way.

Unless stated otherwise, all percentages are intended to be percentages by weight.

EXAMPLES

Preparation of Adjuvant Containing Bars

Benefit agent (e.g., silicone) containing adjuvants of the examples were prepared as follows. Deionized water, water soluble or dispersible fillers (surfactants/fatty acid mixture or Carbowax PEG 2000), skin benefit agent (0.5 micrometer silicone emulsion ex. Dow Corning), and cationic deposition polymers (Jaguar C13S in glycerine dispersion and Merquart 100) were added to a reactor and mixed at 70° C. using an overhead stirrer until all the ingredients either dissolved or dispersed completely to form a uniform mixture. The mixture was then cooled to around room temperature and freeze dried overnight to form free flow solid adjuvants for bar preparation.

Bars containing the above prepared solid adjuvants were prepared first by mixing 15 wt. % of the freeze dried solid adjuvant with 85 wt. % of bar chip in a container. The adjuvant/chip mixture was then extruded through a Sigma Bench Top extruder twice to form logs which were stamped to make example bars of this invention.

Deposition

Deposition of benefit agent (e.g., silicone oil) from bars was determined using Varian Spectra AA600 Atomic Spectroscopy. A 2 inches by 2 inches square strip of porcine skin was prewet with warm tap water and 0.5 ml of water was applied to the skin. The skin was then rubbed with the bar for 15 seconds, lathered for 15 seconds and rinsed with warm running tap water for 10 seconds. It was then wiped once with a paper towel and allowed to dry for 2 minutes. The treated skin was extracted with 10 grams of xylene. The silicone content of xylene extraction was measured by the atomic spectroscopy.

Examples 1 & 2

Benefit Bars

A bar of invention (Examples 1 and 2) and a comparative example bar (comparative example 1) with similar compositions were prepared. Comparative Example 1 has the same composition as Example 1 bar except no cationic deposition polymers was contained in the silicone adjuvant. Example 2 is similar to Example 1 but contains different filler. Another comparative example bar (comparative Example 2) containing both the cationic deposition polymer and the silicone emulsion uniformly distributed in the bar was also prepared. Comparative Example 2 bar was prepared by mixing both the cationic deposition polymer and the silicone emulsion thoroughly with all other bar ingredients to make bar chip (i.e., no separate adjuvant was first prepared). The chip was then extruded and stamped to make comparative Example 2 bars with both the cationic polymer and silicone oil uniformly distributed in the bar rather than concentrated in the adjuvants as Examples 1 and 2 bars (and Comparative 1).

Compositions are set forth below:

TABLE 1

|  | Example 1 | Example 2 | Comparative Example 1 |
|---|---|---|---|
| Composition of Silicone Adjuvants Before Freeze Drying |  |  |  |
| Skin Benefit Agent |  |  |  |
| Silicone Emulsion* | 30 g | 30 g | 30 g |
| Cationic Deposition Polymer |  |  |  |
| Jaguar C13S** | 1 g | 1 g | — |
| MerQuart MQ100 (40%) | 10 g | 10 g | — |
| Water Soluble or Dispersible Filler |  |  |  |
| Surfactant/Fatty Acid Mixture*** | 20 g | — | 20 g |
| Carbowax PEG2000 | — | 20 g | — |
| Other Materials |  |  |  |
| Glycerine | 4 g | 4 g | — |
| Cocoamidopropyl Betaine (30%) | 3.4 g | 3.4 g | 3.4 g |
| Water | to 200 g | to 150 g | to 150 g |
| Composition of Adjuvant-Containing Bars |  |  |  |
| Freeze Dried Silicone Adjuvant | 30 g | 30 g | 25.4 g |
| Premixed Bar Chip**** | 170 g | 170 g | 174.6 g |

Bars of Example 1, Example 2 and Comparative 1 were adjuvant bars. Comparative 2 was a non-adjuvant bar containing 1% Jaguar C13S 5% Silicone oil and 96% bar chip.
*Silicone Emulsion: 60,000 cps silicone oil emulsion 50% solid, 0.5 μm ex. Dow Corning.
**Jaguar C13S: ex. Rhone-Poulenc, Cationic Cellulose.
***74.9% Sodium Cocoyl Isethionate, 21.8% Fatty Acid and 3.0% Sodium Isethionate.
****Bar Chip contains 51.9% Na Cocoyl isethionate, 21.1% stearic acid, 4.90% Na Isethionate, 3.3% coco fatty acid, 11.8% fatty acid sodium soap and other minor ingredients.

Bars made from these compositions were tested for deposition results and results are set forth below.

Deposition of silicone oil of the above prepared bars onto porcine skin was given as follows.

| Example 1 | 3.02 micrograms/cm² of skin |
| Example 2 | 2.89 micrograms/cm² of skin |
| Comparative Example 1 and 2 | <0.2 micrograms/cm² of skin |

The above results clearly shows that deposition of skin benefit agents from the preferred example bars (Examples 1 and 2 prepared first as adjuvants and wherein adjuvants had cationic deposition polymer) onto skin was much higher than for the two comparative examples (i.e., one without cationic deposition aid in adjuvant and one where, rather than making an adjuvant, benefit agent and cationic were uniformly mixed into the composition).

Examples 3–4

Benefit Agent Containing Bars

Additional Examples 3 and 4 were prepared as were Examples 1 and 2. Examples 3 and 4 were again prepared by first preparing an adjuvant chip/powder and then mixing with "regular" surfactant-containing bar chips. Comparatives 3 and 4 different from 3 and 4 only in use of cationic deposition polymer in adjuvant. Compositions are set first in Table 2 below:

TABLE 2

|  | Example 3 | Comparative Example 3 | Example 4 | Comparative Example 4 |
|---|---|---|---|---|
| Composition of Silicone Adjuvants Before Freeze Drying |  |  |  |  |
| Skin Benefit Agent |  |  |  |  |
| Silicone Emulsion* | 50 g | 50 g | — | — |
| Silicone Oil (60,000 cps ex. Dow Corning) |  |  | 25 g | 25 g |
| Deposition Polymer |  |  |  |  |
| MerQuart MQ280 (20%) | 30 g | — | 30 | — |
| Water Soluble or Dispersible Filler |  |  |  |  |
| Carbowax PEG4000 | 44 g | 44 g | 44 g | 44 g |
| Other Materials |  |  |  |  |
| Cocoamidopropyl Betaine (30%) | 3.4 g | 3.4 g | 3.4 g | 3.4 g |
| Water | to 140 g | to 120 g | to 121 g | to 91 g |
| Composition of Adjuvant-Containing Bars |  |  |  |  |
| Freeze Dried Silicone Adjuvant | 30 g | 26.6 g | 30 g | 26.6 g |
| Premixed Bar Chip*** | 170 g | 174.4 g | 170 g | 174.4 g |

*Silicone Emulsion: 60,000 cps silicone oil emulsion 50% solid, 0.5 μm ex. Dow Corning.
***Bar Chip contains 51.9% Na Cocoyl isethionate, 21.1% stearic acid, 4.90% Na Isethionate, 3.3% coco fatty acid, 11.8% fatty acid sodium soap and other minor ingredients.

In these examples another deposition polymer, Merquat 280 (ex. Calgon) which is a highly charged cationic copolymer of dimethyldialkylammonium chloride and acrylic acid, and high viscosity silicone oil (60,000 cps) were used for adjuvant preparation. As noted both the silicone oil adjuvants and example bars were prepared by the methods described in Examples 1–2.

Deposition of silicone of these 4 bars onto porcine skin was determined and given below.

| Example 3 | 2.39 micrograms/cm² of skin |
| Comparative Example 3 | 0.68 micrograms/cm² of skin |
| Example 4 | 5.02 micrograms/cm² of skin |
| Comparative Example 4 | 0.80 micrograms/cm² of skin |

As seen, Example bars 3 and 4 deposited much higher levels of silicone oil than the comparative examples which did not contain cationic polymers in the adjuvants. Again, the criticality of cationic deposition polymer in the adjuvant is clearly shown.

Example 5–7

Adjuvant Containing Low Viscosity Silicone Oil

Examples 5, 6, 7 and comparative Example with composition shown in Table 3 were prepared using the same procedure described in Example 1–2.

TABLE 3

|  | Example 5 | Example 6 | Example 7 | Comparative Example |
|---|---|---|---|---|
| Composition of Silicone Adjuvants Before Freeze Drying | | | | |
| Skin Benefit Agent | | | | |
| Silicone Oil 60,000 cps | 25 g | 25 g | — | 25 g |
| Silicone Oil 1,000 cps | — | — | 25 g | — |
| Cationic Deposition Polymer | | | | |
| Jaguar C13S* | — | 2.5 g | — | — |
| MerQuart MQ100 (20%) | 31.3 g | — | 31.3 g | — |
| Water Soluble or Filler Dispersible | | | | |
| Surfactant/Fatty Acid Mixture** | 40 g | 40 g | 40 g | 40 g |
| Other Materials | | | | |
| Glycerine | — | 7.5 g | — | — |
| Cocoamidopropyl Betaine (30%) | 3.0 g | 3.0 g | 3.0 g | 3.0 g |
| Water | to 156 g | to 175 g | to 156 g | to 125 g |
| Composition of Adjuvant-Containing Bars | | | | |
| Freeze Dried Silicone Adjuvant | 27.4 g | 32 g | 27.4 g | 26.6 g |
| Premixed Bar Chip*** | 172.6 g | 168 g | 172.6 g | 172.6 g |

*Jaguar C13: ex. Rhone-Poulenc, Cationic Cellulose
**74.9% Sodium cocoyl Isethionate, 21.8% Fatty Acid and 3.0% Sodium Isethionate.
***Bar Chip contains 51.9% Na Cocoyl isethionate, 21.1% stearic acid, 4.90% Na Isethionate, 3.3% coco fatty acid, 11.8% fatty acid sodium soap and other minor ingredients.

Deposition of /silicone oil onto porcine skin from these bars is summarized below.

| Example 5 | 1.58 micrograms/cm² of skin |
| Example 6 | 2.51 micrograms/cm² of skin |
| Example 7 | 2.03 micrograms/cm² of skin |
| Comparative Example 5 | 0.25 micrograms/cm² of skin |

Example 7, which contained a lower viscosity silicone oil (1,000 cps ex. Dow Corning) than the one used for Example 5, 6 and comparative Example 5, deposited about the same amount of silicone oil as Examples 5 and 6 and deposited much more than the comparative Example 5. These examples shows that deposition of skin benefit agent from bars containing the preferred adjuvants is not dependent on the viscosity of the skin benefit agents.

Example 8–10

Solid Skin Benefit Agents

A solid skin benefit agent, stearic acid, was used to prepare example bars of this invention. A stearic acid emulsion containing 49.5% stearic acid particles and 1 wt. % of Cocoamido propyl betaine was prepared using a Ross mixer equipped with homogenizer, 4-blade mixer and scrapper. 2,021 grams of fatty acid was added to 2,061 grams of 2% Cocamido propyl betaine solution and was emulsified at 70° C. The prepared emulsion had needle type crystals with particle size about 37.5 micrometers as determined by Malvern Particle Size.

Bar composition of Example 8–10 and comparative Example 8 is shown in Table 4 below.

TABLE 4

|  | Example 8 | Example 9 | Example 10 | Comparative Example 8 |
|---|---|---|---|---|
| Composition of Silicone Adjuvants Before Freeze Drying | | | | |
| Skin Benefit Agent | | | | |
| Stearic Acid Emulsion | 90 g | 90 g | 90 g | 180 g |
| Deposition Polymers | | | | |
| 3% Jaguar C13S Solution | 99 g | — | — | — |
| 10% MerQuat 100 Solution | — | 29.7 | — | — |
| 40% MerQuat 100 Solution | — | — | 29.7 | — |
| Composition of Adjuvant-Containing Bars | | | | |
| Freeze Dried FA Adjuvant | 32 g | 32 g | 38 g | 30 g |
| Bar Chip* | 168 g | 168 g | 162 g | 170 g |

*Bar Chip contains 27.3% Sodium Cocoyl Isethionate, 9.18% Palmitic/Stearic acid mixture, 33.9% Carbowax PEG 8000, 2.46% Sodium Isethionate, 5.1% Sodium Cocoamidopropyl Betaine with 15% hole.

Fatty acid adjuvants of Examples 8, 9 and 10 were prepared by mixing the fatty acid emulsion with deposition polymer solution at room temperature using a Hobart Kitchen Aid Mixer for about 30 minutes. The fatty acid/polymer mixture were then freeze dried to form free flow fatty acid adjuvants. Fatty acid adjuvant of comparative Example 8 was prepared by freeze drying the fatty acid emulsion. Bars containing these fatty acid adjuvants were prepared by the same process described in Examples 1–2.

Deposition of fatty acid from these bars onto porcine skin was determined using GC. Skin was treated with bar using the same procedure described in Example 1 except 10 grams of heptane instead of xylene was used for extraction. Deposition of fatty acid onto skin from these bars is given below:

| Example 8 | 3.41 micrograms/cm² of skin |
| Example 9 | 4.95 micrograms/cm² of skin |
| Example 10 | 9.86 micrograms/cm² of skin |
| Comparative Example 8 | 2.5 micrograms/cm² of skin |

This data shows that deposition of solid benefit agent from bar can also be enhanced using the adjuvants of the invention.

I claim:

1. A two-step method for preparing a detergent bar composition having enhanced deposition of a benefit agent which method comprises:

(1) preparing a dried adjuvant composition by mixing component (a), (b) and (c) below and from about 9% to about 66% by wt. water to form a uniform aqueous mixture comprising benefit agents having a particle size of from about 0.1 µm to about 100 µm, and subsequently drying said aqueous mixture to prepare said dried adjuvant; wherein said dried adjuvant composition comprises, by wt. of said dried adjuvant composition;

(a) 20% to 96% benefit agent;
(b) 2 to 40% cationic deposition polymer;
(c) 0 to 78% water soluble or water dispersible filler; and
(d) 0 to 15% water; and (2) thereafter mixing said dried adjuvant composition with a separately prepared base bar chip composition comprising a surfactant system to form a bar composition comprising:

(I) 5 to 50% by wt. of said dried adjuvant chip composition; and
(II) 50 to 95% by wt. of base bar chip composition;

wherein said benefit agent (1)(a) is selected from the group consisting of: silicone oils, silicone gums and modifications thereof; fats and oils; waxes; hydrophobic plant extracts; hydrocarbons; fatty acids; alcohols; esters; essential oils; lipids; vitamins; sunscreens; and mixtures of any of the foregoing components.

2. A method according to claim 1, wherein benefit agent in said dried adjuvant composition comprises 30% to 60%.

3. A method according to claim 1, wherein cationic deposition polymer comprises 5% to 30% of said dried adjuvant composition.

4. A method according to claim 1, wherein the surfactant system of the base bar chip composition comprises:

(a) a first anionic surfactant; and
(b) a second surfactant selected from the group consisting of second anionic surfactant different from the first, a nonionic, an amphoteric and mixtures thereof.

5. A method according to claim 4, wherein the first anionic surfactant of the base bar chip composition is acyl isethionate.

6. A method according to claim 5, wherein the isethionate is from 10% to 90% by wt. of the base bar chip composition.

7. A method according to claim 4, wherein the second surfactant of said base bar chip composition is sulfosuccinate.

8. A method according to claim 4, wherein the second surfactant of said base bar chip composition is betaine.

9. A method according to claim 8, wherein the second surfactant of said base bar chip composition is amidocococoylbetaine.

10. A method according to claim 4, wherein the second surfactant comprises a mixture of sulfosuccinate and betaine.

* * * * *